United States Patent [19]

Cordia

[11] Patent Number: 5,511,854
[45] Date of Patent: Apr. 30, 1996

[54] HEAD SUPPORT AND FEEDING AID

[76] Inventor: James M. Cordia, Rte. 1, Box 211, Oakridge, Mo. 63769

[21] Appl. No.: 262,499

[22] Filed: Jun. 20, 1994

Related U.S. Application Data

[63] Continuation-in-part of Ser. No. 84,492, Jul. 1, 1993, Pat. No. 5,395,158.

[51] Int. Cl.$^6$ ............................................. A47C 7/38
[52] U.S. Cl. .................... 297/393; 297/DIG. 6; 297/DIG. 4
[58] Field of Search ................... 297/391, 393, 297/464, DIG. 4, DIG. 6; 602/17; 248/316.6, 316.1; 280/304.1

[56] References Cited

U.S. PATENT DOCUMENTS

| | | | |
|---|---|---|---|
| 2,638,293 | 5/1953 | Lindstrom | 244/122 |
| 2,796,866 | 6/1957 | Cohen | 128/303 |
| 2,949,152 | 8/1960 | Hipps et al. | 155/28 |
| 3,188,079 | 6/1965 | Boetcker et al. | 269/328 |
| 3,359,976 | 12/1967 | Laval, Jr. | 602/17 X |
| 3,372,491 | 3/1968 | Morrison | 34/99 |
| 3,497,259 | 2/1970 | Sherfey | 297/391 |
| 3,657,774 | 4/1972 | Reynolds | 24/73 CF |
| 3,730,589 | 5/1973 | Lane | 297/391 |
| 3,897,777 | 8/1975 | Morrison | 128/133 |
| 3,957,262 | 5/1976 | McReynolds | 269/328 |
| 4,182,322 | 1/1980 | Miller | 128/133 |
| 4,227,740 | 10/1980 | East | 297/310 |
| 4,339,151 | 7/1982 | Riggs | 297/464 |
| 4,589,407 | 5/1986 | Koledin et al. | 128/87 R |
| 4,607,885 | 8/1986 | del Fierro | 297/397 |
| 4,707,031 | 11/1987 | Meistrell | 297/393 |
| 4,989,836 | 2/1991 | Hudson, III et al. | 297/391 |
| 5,010,898 | 4/1991 | de Kanawati et al. | 602/17 X |
| 5,081,714 | 1/1992 | Liu | 297/393 X |
| 5,306,232 | 4/1994 | Whitmyer | 602/17 X |

FOREIGN PATENT DOCUMENTS

| 389309 | 9/1990 | European Pat. Off. | 248/315 |
|---|---|---|---|

*Primary Examiner*—Milton Nelson, Jr.
*Attorney, Agent, or Firm*—Jacobson, Price, Holman & Stern

[57] ABSTRACT

A head support and feeding aid is provided for a wheelchair patient whose head slumps forwardly when seated. A headband is attached to a frame on the wheelchair seat back by an adjustable cord. By progressively adjusting the length of the cord, the headband progressively lifts the patient's head to a more and more upright position. The length of the cord is adjusted by a releasable cord clamp behind the frame.

19 Claims, 5 Drawing Sheets

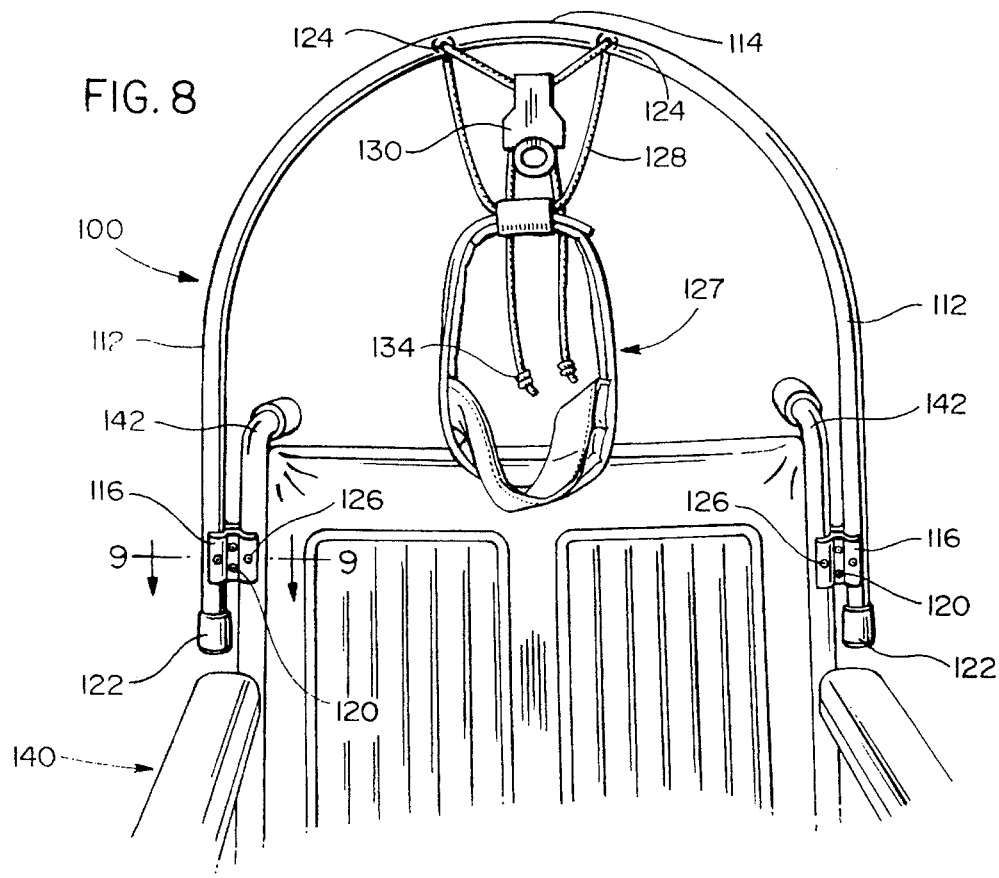
FIG. 8
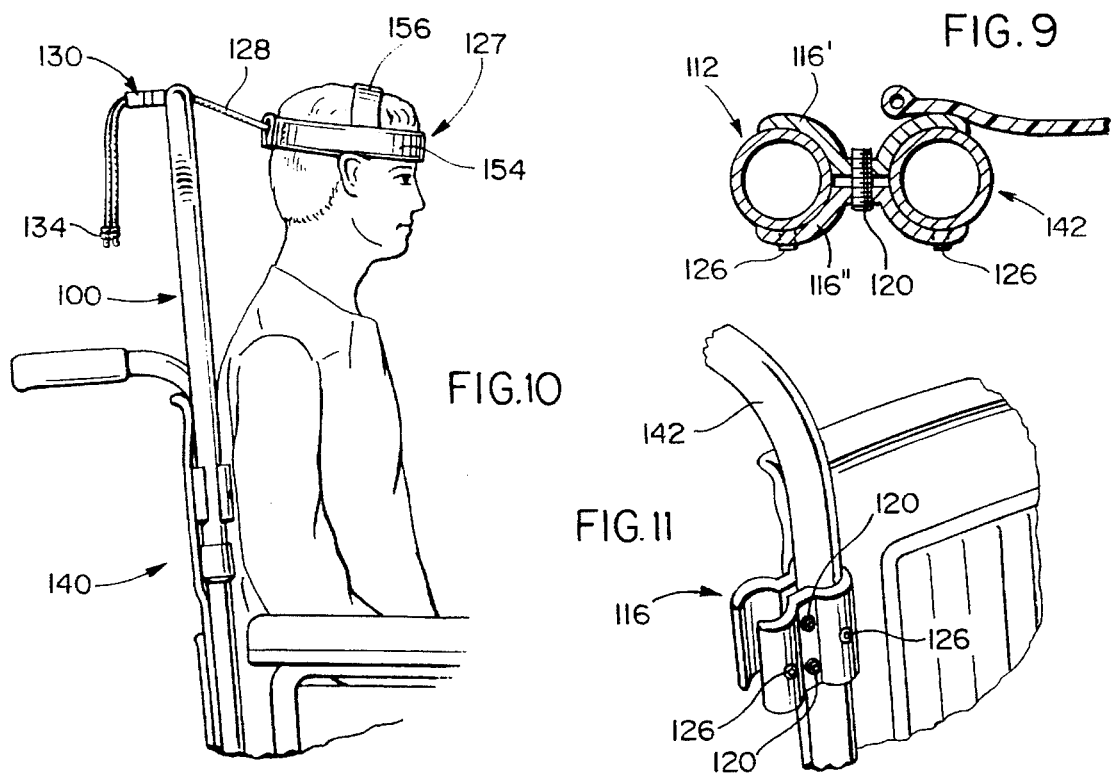
FIG. 9
FIG. 10
FIG. 11

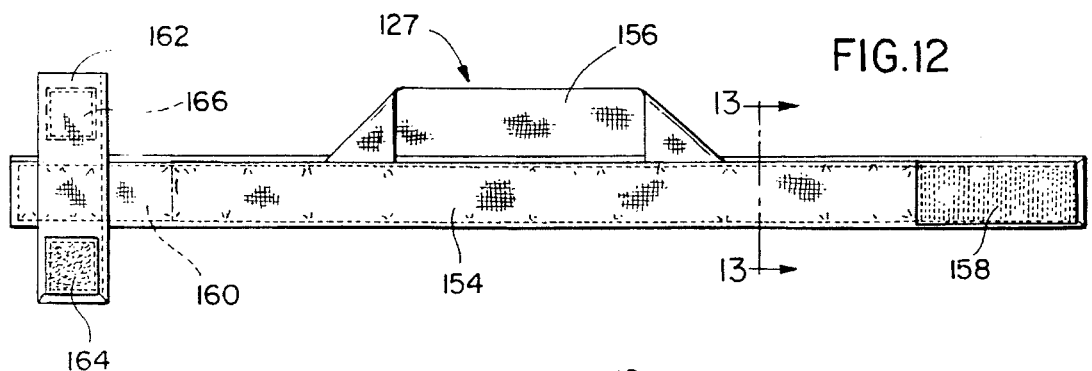
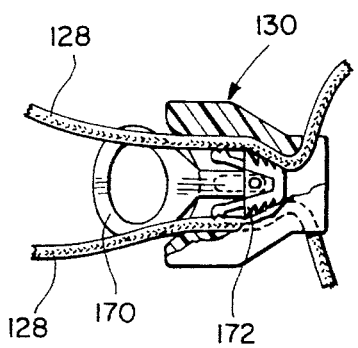
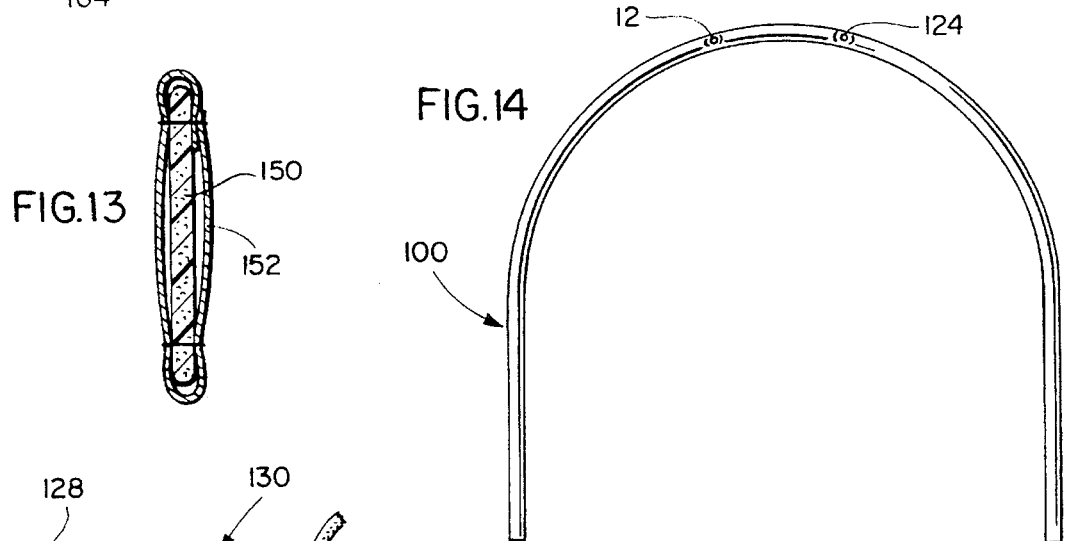

HEAD SUPPORT AND FEEDING AID

This application is a continuation-in-part of application Ser. No. 08/084,492, filed Jul. 1, 1993, now Pat. No. 5,395,158.

BACKGROUND OF THE INVENTION

This invention relates to an adjustable head support and feeding aid for patients who have lost muscle control in the back, shoulders or neck region to the extent that, when seated, the patient's head tends to slump forwardly towards or even onto the chest.

Many wheelchair patients, for example, lose the ability to control head movement. Shoulder and neck muscles become weak from non-movement and deteriorate rapidly to the extent that the patient is unable to hold the head upright and it tends to slump forwardly onto the chest. This condition is accelerated in older patients, particularly where the patient's condition has been weakened from prior medical problems such as stroke, or arthritis. Once the neck muscles weaken and the head drops forward, breathing becomes more difficult, and the intake of food and drink is impaired.

SUMMARY OF THE INVENTION

It is an object of the invention to provide a head support and feeding aid for patients of the above kind, which is useful in supporting the head in a more upright position and which with extended use may even be useful in restoring a degree of muscle power enabling the patient more readily to provide self-support for the head.

Another object of the invention is to provide a head support and feeding aid as described which can be adjusted in use, so that the patient's head can be brought gradually, over a period of time, to a more and more upright position.

A further object of the invention is to provide a head support and feeding aid in the form of an attachment which can be readily secured to a wheelchair or other seat.

A still further object of the invention is to provide a head support and feeding aid which is comfortable to wear and allows substantially unrestricted movements of the head other than in a forward direction.

Yet a further object of the invention is to provide a head support and feeding aid which is simple in design, economical to manufacture and easy to use.

In fulfillment of the above, a head support and feeding aid according to the invention, at least in a preferred embodiment thereof, comprises an arch-like support frame adapted to be attached to the back of a wheelchair or other seat so that the top of the frame extends substantially to the level of a seated patient's head, a headband of suitably soft and pliable material adapted to fit around the patient's forehead, an attachment cord or the like extending from each end of the headband through apertures in the frame, and releasable clamps on the cord behind the frame for adjusting the distance of the headband from the frame to suit the patient's head position and whereby the distance can be decreased to draw the patient's head progressively to a more and more upright position.

The frame may have adjustment means for height to suit a patient's height and head position and it may additionally have attachment means at its base for securing the frame to different size wheelchairs.

With extended use of the apparatus, a patient's head can be progressively brought to a more and more upright position with attendant beneficial effects.

Additional features and advantages of the invention will become apparent from the ensuing description and claims read in conjunction with the attached drawings.

BRIEF DESCRIPTION OF DRAWINGS

FIG. 8 is a front elevational view of a further embodiment of the head support and feeding aid according to the invention, FIG. 9 is a cross-sectional view taken along lines 9—9 of FIG. 8 illustrating one of the attachment clamps, FIG. 10 is a side elevational view of the wheelchair showing the head support and feeding aid of FIG. 8 in use, FIG. 11 is a side perspective view of a part of a wheelchair with the attachment clamp of FIG. 8 attached, FIG. 12 is a front elevational view of the headband, FIG. 13 is a cross-sectional view taken along lines 13—13 of FIG. 12, FIG. 14 is a front elevational view of the attachment frame of FIG. 8, FIG. 15 is a partial, cross-sectional side view of the releasable clamp illustrated in FIG. 8, and FIG. 16 is a side perspective view of the headband with the cord being attached.

DESCRIPTION OF PREFERRED EMBODIMENTS

Figure 1:
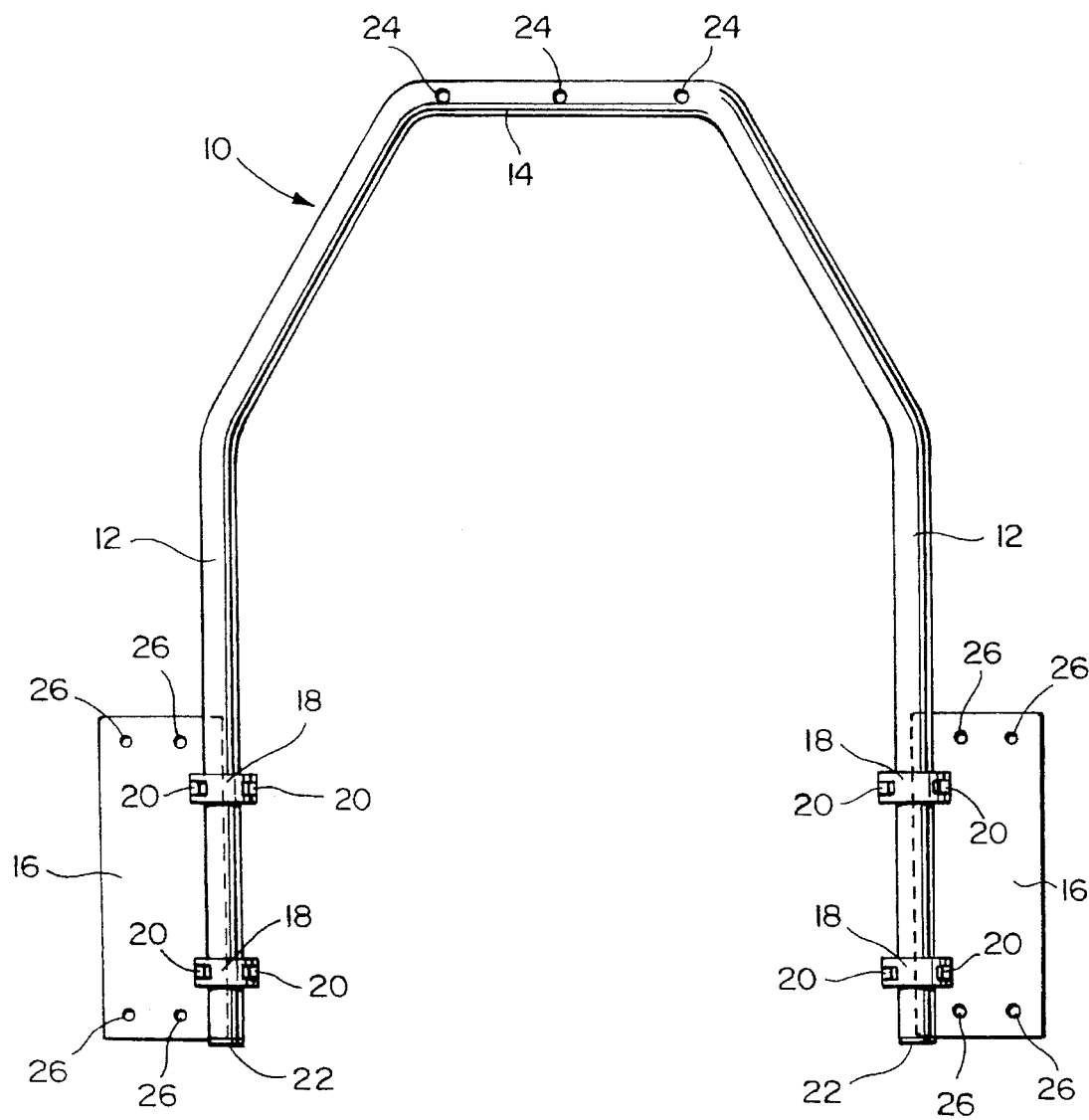
FIG. 1 is a rear elevational view of an attachment frame for a head support and feeding aid according to the invention.
Figure 2:
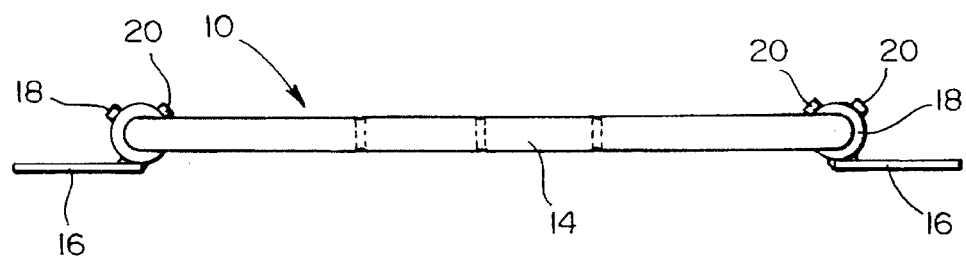
FIG. 2 is a plan view of the frame.
Figure 3:
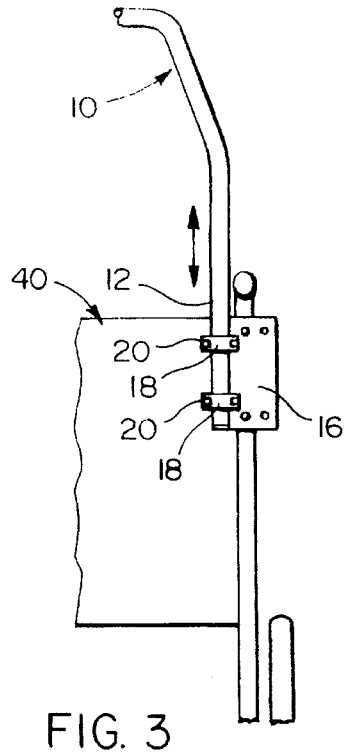
FIG. 3 is a rear elevational view of a part of a wheelchair with the frame attached.

An attachment frame 10 for a head support according to the invention is shown in detail in FIGS. 1 and 2. The frame is substantially in the shape of an arch with legs 12, and an upper cross-bar or limb 14. Preferably the frame is made of metal tubing or the like. At the bottom of each leg, the frame carries an attachment plate or bracket 16 mounted on the respective leg by a pair of collars 18 welded to the plate. The legs 12 are free to move lengthwise in the collars which are provided with tightening screws 20 for tightening down and locking against the frame. The bottom of each leg has a stop 22. Apertures 24 are provided through the limb 14 and inner and outer pairs of apertures 26 are provided in plates 16. (In an alternative embodiment, the frame 10 can be made of wood and can have attachment apertures at the bottom of each leg, eliminating the plates 16 and collars 18.)

Figure 4:
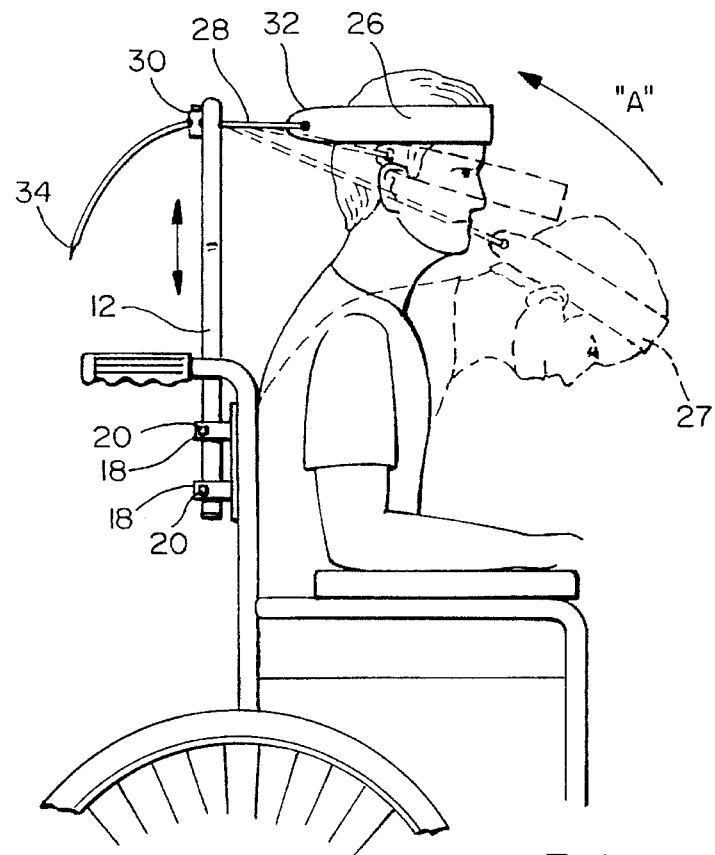
FIG. 4 is a side elevational view of the wheelchair showing the head support and feeding aid in use.
Figure 5:
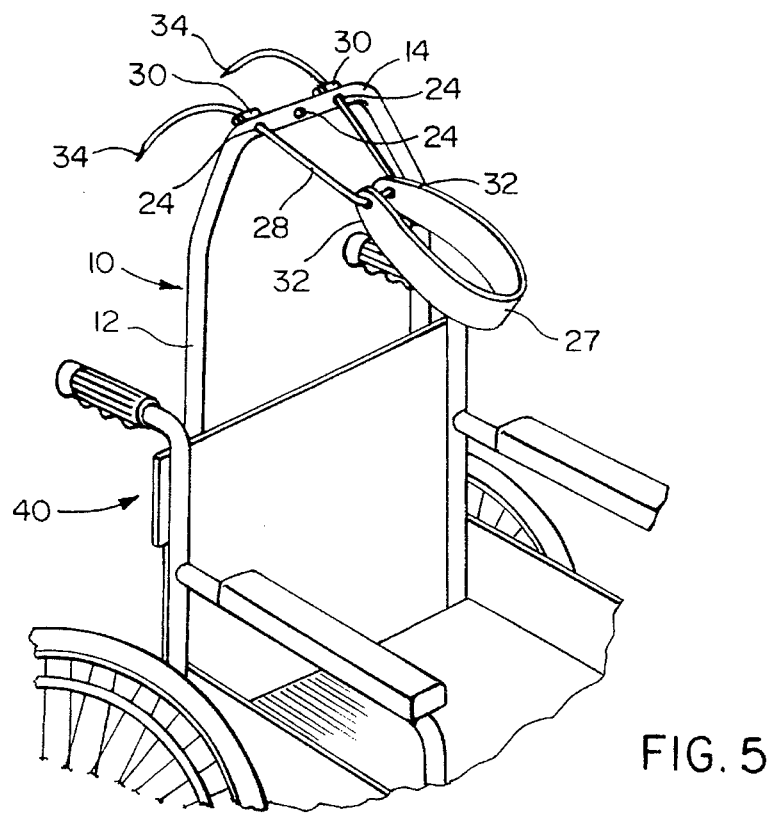
FIG. 5 is a front perspective view of the wheelchair and attached head support.

The apparatus further includes a headband 27, see FIGS. 4 and 5, a cord 28, and releasable clamps 30 for the cord. The headband may be of any suitable soft and flexible material for example foam rubber or the like in a fabric or terry-cloth cover, and has eyes 32 at each tapered end for the cord. The cord may comprise a length of plastic tubing with tapered ends 34. The ends of the cord are inserted from the front through the outer apertures 24 in frame 10, and are held in place behind the frame by the clamps 30. The clamps may, for example, comprise any known form of tube or cord clamp, for example, of the spring loaded plunger type. (In an alternative embodiment, the opposite ends of the headband may be secured to a single cord which is inserted through central aperture 24 and secured behind the frame by a single clamp.)

In use, the frame 10 is secured to the back of the wheelchair 40 using either the inner or outer set of apertures 20, depending on the width of the chair back. The height of the frame is adjusted in collars 18 so that the cross bar 14 is substantially level with a patient's forehead when the patient is seated upright, and the frame is locked in place using screws 20. Initially, the patient's head will drop forward to the dotted line position shown in FIG. 4. The headband is fitted around the patient's forehead and cord 28 is initially adjusted using clamps 30 so that the headband exerts minimum upward pressure to the head in the direction of arrow A, for example lifting the head about one inch. Gradually, over a period of days, the cord can be adjusted through clamps 30, to reduce the distance between the headband and frame 10, thereby lifting the patient's head progressively in increments into a more and more upright position.

The head support is thus useful in helping to feed a patient and also to help the patient gradually regain an upright posture. Moreover, during use, the patient retains substantially unrestricted head movements other than in a downward direction. Extended use of the device assists in feeding the patient and also assists the patient in attaining improved breathing and posture. With extended use, the patient may even recover sufficient muscle control to sit unaided in a more upright position.

Figure 6:
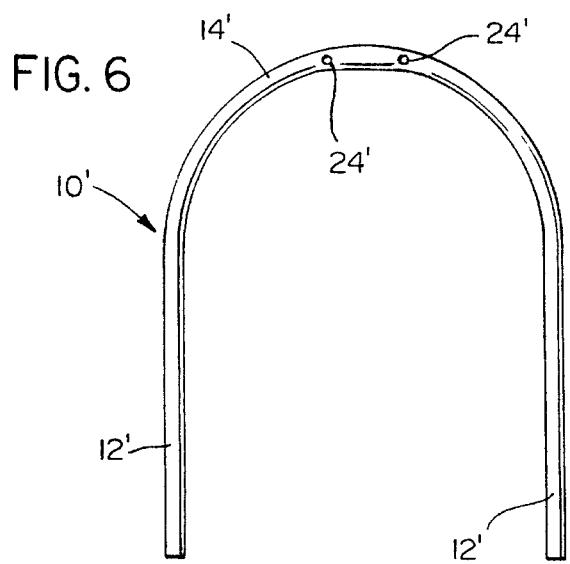
FIG. 6 is an elevational view of a simplified attachment frame.
Figure 7:
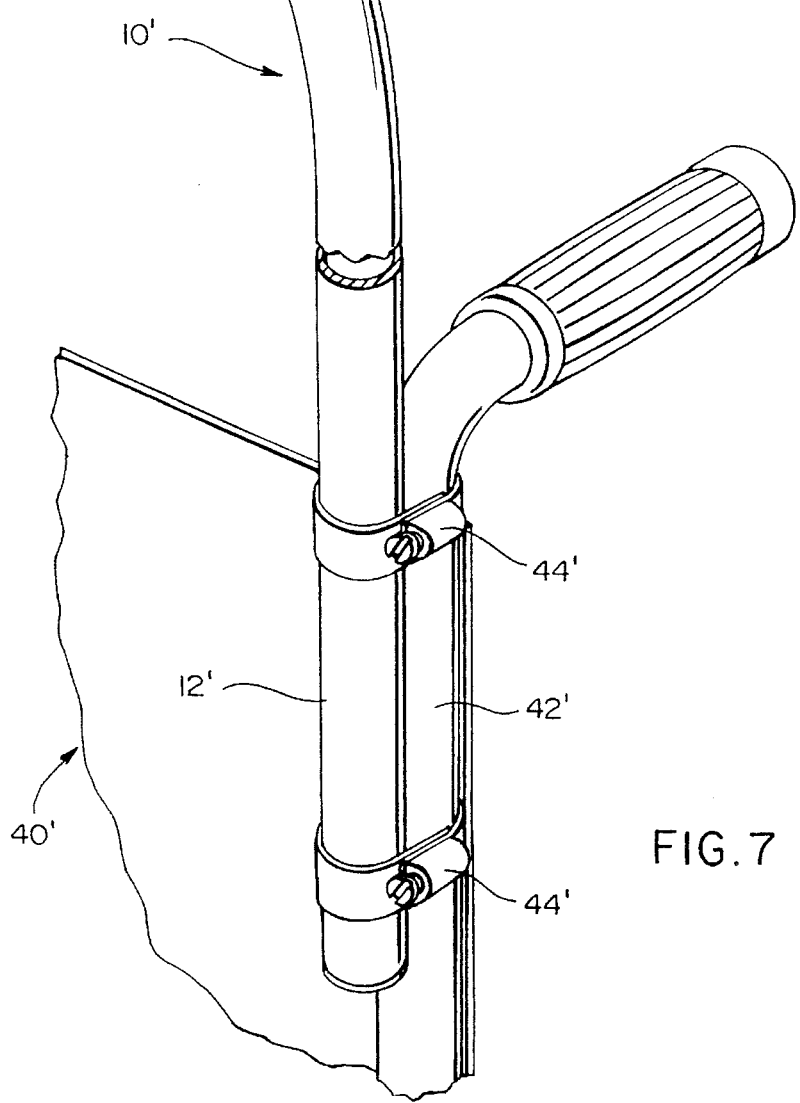
FIG. 7 is an enlarged perspective view of part of a wheelchair showing an attachment for the simplified frame.

FIGS. 6 and 7 show a simplified attachment frame 10' which has a smoother continuous curve-like arch with an upper limb 14', legs 12' and apertures 24' as previously. The frame is again made of metal tubing and attaches to the side frames 42' of a wheelchair 40' by hose clips 44'. The hose clips again allow for height adjustment of frame 10'. The headband and cords are attached through apertures 24' as previously and the apparatus is used in like manner.

In another and most preferred embodiment illustrated in FIGS. 8–16, an attachment frame 100 is shown particularly in FIGS. 8 and 14. The frame, preferably made of metal tubing, is substantially in the shape of a smooth continuous curve-like arch as in FIG. 6 with legs 112 and an upper limb 114. The frame 100 attaches to the side frames 142 of the wheelchair 140 by conventional attachment clamps 116 shown in FIGS. 8, 9 and 11. The attachment clamps 116 are bilateral and formed of two matching halves 16' and 116". The attachment clamps 116 have cap screws 120 for tightening down and locking against the frame 100 and side frames 142 of the wheelchair 140. The attachment clamps also have set screws 126 for providing a similar function. The attachment clamps are illustrated for convenience shown attached to tubing of equal size; however, the attachment clamps preferably accommodate a nominal 1" side frame 142 of the wheelchair 140 and a nominal ¾ "frame 100. The attachment clamps allow for height adjustment of frame 100 in similar manner to the other embodiments. The bottom of each leg has a stop 122. Apertures 124 are provided through limb 114.

The apparatus further includes a headband 127 shown in FIGS. 8, 10, 12, 13 and 16, a cord 128 shown in FIGS. 8, 10, 15 and 16, and a releasable clamp 130 for the cord 128 shown in FIGS. 8 and 15. The headband may be of any suitable soft and flexible material, for example, batting 150 or the like in a fabric 152. Headband 127 has portion 154 which fits around the patient's forehead and a portion 156 which fits around the patient's head as illustrated in FIG. 10. The headband 127 is adjustable in circumference and includes hook fabric 158 and loop fabric 160 at opposite ends of portion 154. The headband 127 also has a flap 162 which includes hook fabric 164 and loop fabric 166 for attaching the cord 128.

The cord 128 preferably comprises a length of nylon braided cord of suitable diameter, preferably ³⁄₁₆". The ends 134 of the cord 128 are inserted from the front through the apertures 124 in frame 100, and are held in place behind the frame by the clamp 130. The ends 134 of the cord may be knotted after insertion through apertures 124 as illustrated in FIGS. 8 and 10. The clamp 130 is a conventional cord lock which includes a ring pull slide 170 having self-locking feelers 172.

In use, the frame 100 is secured to the back of the wheelchair 140 using attachment clamps 116. The height of the frame 100 is adjusted so that the limb 114 is substantially level with a patient's forehead when the patient is seated upright, and the frame is locked in place using cap screws 120 and set screws 126. The portion 154 of headband 127 is adjusted to a comfortable fit of the patient's head, closing the hook fabric 158 and loop fabric 160 of portion 154 securely. It is recommended that there is two finger's space between the patient's head and the headband. The cord 128 is then attached to the headband 127 using flap 162 as illustrated in FIG. 16 at the centerpoint of the cord loop. The hook fabric 164 and loop fabric 166 should be fastened securely around the cord 128. The headband 127 is then fitted around the patient's forehead and cord 128 is initially adjusted using clamp 130 so that the headband exerts minimum upward pressure to the head.

While only preferred embodiments of the invention have been described herein in detail, the invention is not limited thereby and modifications can be made within the scope of the attached claims.

I claim:

1. A head support and feeding aid for a patient whose head slumps forward when seated comprising a frame having a lower part for attachment to a seat back and an upper limb part, said upper limb part including aperture means formed therein, a headband for fitting around a patient's forehead, the headband having means for adjusting its circumference, cord means extending from the headband for insertion through the aperture means in the upper limb part of the frame, and releasable clamp means on the cord means for adjusting a length of the cord means between the headband and the frame thereby adjusting the distance of the headband from the frame to suit a patient's head position and whereby said length and said distance can be decreased progressively to draw a patient's head progressively to a more and more upright position.

2. A head support and feeding aid as claimed in claim 1, wherein the means for adjusting the circumference of the headband is cooperating hook and loop fabric.

3. A head support and feeding aid as claimed in claim 1, wherein the headband has means for attaching the cord means comprising flap means with cooperative hook and loop fabric means.

4. A head support and feeding aid as claimed in claim 1, wherein the releasable clamp means comprises a releasable clamp attached to each end of the cord means.

5. A head support and feeding aid as claimed in claim 1, wherein the cord means comprises a nylon braided cord.

6. A head support and feeding aid as claimed in claim 1, wherein the cord means comprises plastic tubing and wherein the releasable clamp means comprises at least one clamp.

7. A head support and feeding aid as claimed in claim 6, wherein the tubing has tapered ends.

8. A head support and feeding aid as claimed in claim 1, wherein the frame has depending legs, and attachment means for securing the legs to a seat back.

9. A head support and feeding aid as claimed in claim 8, wherein the attachment means includes height adjustment means for the frame.

10. A head support and feeding aid as claimed in claim 9, wherein the attachment means for each leg comprises a plate with plural apertures to receive connectors, and the height adjustment means comprises at least one releasable locking collar on the plate in which a respective leg of the frame is received.

11. A head support and feeding aid as claimed in claim 9, wherein the attachment means for each leg comprises at least one hose clamp.

12. A head support and feeding aid as claimed in claim 9, wherein the attachment means for each leg comprises a bilateral clamp having screw means for attaching each leg to a side frame of a wheelchair.

13. A wheelchair for a patient whose head slumps forward when seated, the wheelchair having a frame attached thereto, the frame having aperture means, a headband for fitting around a patient's forehead, the headband having means for adjusting its circumference, cord means extending from the headband through the aperture means in the frame, and releasable clamp means on the cord means for adjusting a length of the cord means between the headband and the frame whereby the headband, cord means and clamp means can be used as a head support for a patient for lifting the patient's head to a more upright position.

14. A wheelchair as claimed in claim 13, including height adjustment means for the frame.

15. A wheelchair as claimed in claim 13, wherein the frame is attached to the wheelchair by attachment means comprising a bilateral clamp having screw means for attaching each leg to a side frame of the wheelchair.

16. A wheelchair as claimed in claim 13, wherein the means for adjusting the circumference of the headband is cooperating hook and loop fabric.

17. A wheelchair as claimed in claim 13, wherein the headband has means for attaching the cord means comprising flap means with cooperative hook and loop fabric.

18. A wheelchair as claimed in claim 13, wherein the releasable clamp means comprises a releasable clamp attached to each end of the cord means.

19. A wheelchair as claimed in claim 13, wherein the cord means comprises a nylon braided cord.

\* \* \* \* \*